(12) United States Patent
Katkar

(10) Patent No.: US 10,959,710 B2
(45) Date of Patent: Mar. 30, 2021

(54) SUCTION DEVICES AND METHODS FOR FINE NEEDLE ASPIRATION

(71) Applicant: FNAPEN LLC, San Antonio, TX (US)

(72) Inventor: Amol Suryakant Katkar, San Antonio, TX (US)

(73) Assignee: FNAPEN LLC, San Antonio, TX (US)

(*) Notice: Subject to any disclaimer, the term of this patent is extended or adjusted under 35 U.S.C. 154(b) by 329 days.

(21) Appl. No.: 15/777,265

(22) PCT Filed: Oct. 31, 2016

(86) PCT No.: PCT/US2016/059648
§ 371 (c)(1),
(2) Date: May 18, 2018

(87) PCT Pub. No.: WO2017/087143
PCT Pub. Date: May 26, 2017

(65) Prior Publication Data
US 2018/0325503 A1    Nov. 15, 2018

Related U.S. Application Data

(60) Provisional application No. 62/257,843, filed on Nov. 20, 2015.

(51) Int. Cl.
*A61B 10/02* (2006.01)

(52) U.S. Cl.
CPC ...... *A61B 10/0283* (2013.01); *A61B 10/0233* (2013.01); *A61B 10/0266* (2013.01); *A61B 2010/0208* (2013.01)

(58) Field of Classification Search
CPC ............ A61B 10/0283; A61B 10/0233; A61B 10/0266; A61B 2010/0208; A61B 17/3494; A61B 2090/062; A61B 90/06
See application file for complete search history.

(56) References Cited

U.S. PATENT DOCUMENTS

| 4,287,819 A | 9/1981 | Emerit |
| 4,549,554 A | 10/1985 | Markham |
| 4,640,297 A | 2/1987 | Bates |
| 4,697,600 A | 10/1987 | Cardenas et al. |

(Continued)

FOREIGN PATENT DOCUMENTS

| CN | 203107781 | 8/2013 |
| CN | 204542231 | 8/2015 |

(Continued)

OTHER PUBLICATIONS

Brown, Jeremy Scott, Nisha Naresh Patel, and Simranjit Singh Rekhi. "Design of a Novel Device for Fine Needle Aspiration." (2013).

(Continued)

*Primary Examiner* — Patrick Fernandes
(74) *Attorney, Agent, or Firm* — Parker Highlander PLLC

(57) ABSTRACT

Suction devices and methods for fine needle aspiration. Certain embodiments include an inner tubular member and a piston disposed within an outer cylinder. In particular embodiments, a vacuum is created in a portion of the interior volume of the outer cylinder and in the interior volume of the inner tubular member when the piston is moved toward the distal end of the inner tubular member.

18 Claims, 4 Drawing Sheets

(56) References Cited

U.S. PATENT DOCUMENTS

| | | | |
|---|---|---|---|
| 4,766,907 A | 8/1988 | De Groot et al. | |
| 4,967,762 A | 11/1990 | Devries | |
| 4,989,614 A * | 2/1991 | Dejter, Jr. | A61B 10/0283 600/565 |
| 5,213,110 A * | 5/1993 | Kedem | A61B 10/0275 600/567 |
| 5,492,130 A | 2/1996 | Chiou | |
| 5,916,175 A | 6/1999 | Bauer | |
| 5,951,489 A | 9/1999 | Bauer | |
| 6,228,039 B1 | 5/2001 | Binmoeller | |
| 6,402,701 B1 | 6/2002 | Kaplan et al. | |
| 7,037,276 B2 | 5/2006 | Sayet et al. | |
| 7,497,833 B2 | 3/2009 | Miller | |
| 7,766,843 B2 | 8/2010 | Voegele | |
| 7,927,288 B2 | 4/2011 | Gianchandani et al. | |
| 8,162,851 B2 | 4/2012 | Heske et al. | |
| 8,287,465 B2 | 10/2012 | Hardin et al. | |
| 8,679,032 B2 | 3/2014 | Mark et al. | |
| 8,728,045 B2 | 5/2014 | Hu et al. | |
| 8,808,200 B2 | 8/2014 | Miller et al. | |
| 8,858,463 B2 | 10/2014 | Seiger et al. | |
| 9,060,760 B2 | 6/2015 | Sullivan et al. | |
| 9,161,743 B2 | 10/2015 | McCullough et al. | |
| 2002/0082518 A1 | 6/2002 | Weiss et al. | |
| 2005/0228312 A1 | 10/2005 | Surti | |
| 2011/0066075 A1 | 3/2011 | Van Bladel et al. | |
| 2013/0060160 A1 | 3/2013 | Heier | |
| 2013/0165815 A1 | 6/2013 | Zinn et al. | |
| 2013/0172777 A1 | 10/2013 | Kwon | |
| 2015/0018712 A1 | 1/2015 | Seiger et al. | |
| 2015/0057571 A1 | 2/2015 | Gundberg | |
| 2015/0190124 A1 | 7/2015 | McCullough et al. | |

FOREIGN PATENT DOCUMENTS

| | | |
|---|---|---|
| EP | 0010321 | 4/1980 |
| EP | 0709060 | 5/1996 |
| EP | 0780089 | 6/1997 |
| EP | 0983749 | 5/2005 |
| EP | 0983021 | 8/2006 |
| KR | 20150021633 | 10/2015 |
| WO | WO 2015/066621 | 5/2015 |

OTHER PUBLICATIONS

Partial Supplementary European Search Report issued in corresponding European Patent Application No. 16866836.6, dated May 24, 2019.

European Search Report issued in European Application No. 16866836.6, dated Aug. 28, 2019.

* cited by examiner

SUCTION DEVICES AND METHODS FOR FINE NEEDLE ASPIRATION

This application is a national phase application under 35 U.S.C. § 371 of International Application No. PCT/US2016/059648, filed Oct. 31, 2016, which claims the benefit of U.S. Provisional Patent Application No. 62/257,843, filed Nov. 20, 2015, the entirety of each of which is incorporated herein by reference.

BACKGROUND INFORMATION

Several factors can affect a sample yield during a fine needle aspiration (FNA). For example, the amount of sample obtained from FNA procedures can depend on several qualities of excursions including the velocity, the total number of excursions, and the depth of the excursion.

Existing systems and methods for FNA procedures can lead to inconsistent results due to variations in these qualities and other factors.

Accordingly, there exists a need for devices and methods to provide precise, accurate FNA procedures to increase the quality and volume of sample yields.

SUMMARY

Exemplary embodiments of the present disclosure comprise a device configured to allow a user to create a vacuum during a fine needle aspiration (FNA) procedure. The vacuum is created without the need for external components and can be used to increase the yield of material obtained during the procedure.

Exemplary embodiments also allow a user to precisely control the depth of penetration of instruments used during medical procedures, including for example FNA. With typical FNA procedures, it is difficult for a user to control the motion of their fingers and wrists in order to get an adequate specimen. This can result in a failed FNA procedure, leading to patient frustration and repeated attempt which can increase the cost of the procedure (in both time and money) to the patient, physician, and institute. In addition, lack of instrument control can lead to poor samples contaminated by blood which are not suitable for analysis.

As explained more fully below, embodiments of the present disclosure can allow a user to increase the speed and depth of the instrument penetration during FNA or other procedures. This can increase the amount of tissue taken during the sample and decrease the contamination of the sample by blood.

Certain embodiments include a device for fine needle aspiration comprising: an inner tubular member comprising a proximal end and a distal end; an outer tubular member disposed around the inner tubular member, where the outer tubular member comprises a proximal, a distal end, and a plurality of slots; an outer housing disposed around the outer tubular member, where the outer housing comprises a proximal end and a distal end; a biasing member disposed between the outer tubular member and the outer housing; and a rod coupled to the inner tubular member. In particular embodiments: the rod extends through the outer tubular member; the rod is configured to be moved from a first slot in the plurality of slots to a second slot in the plurality of slots; the first slot is a first distance from proximal end of the housing; the second slot is a second distance from the proximal end of the housing; and the biasing member is configured to bias the housing away from the rod.

In specific embodiments, the rod is coupled to the inner tubular member via a collar that extends around the inner tubular member. In certain embodiments, the collar is configured for axial and radial sliding engagement with the inner tubular member. In particular embodiments, the outer tubular member comprises a projection that engages the biasing member. In some embodiments, the proximal end of the housing is configured to engage the projection when the biasing member is in an expanded configuration, and the proximal end of the housing is configured to engage the rod when the biasing member is in a compressed configuration.

In specific embodiments, the outer tubular member extends a first distance from the distal end of the outer housing when the biasing member is in an expanded configuration; the outer tubular member extends a second distance from the distal end of the outer housing when the biasing member is in a compressed configuration; and the first distance is less than the second distance.

In certain embodiments, the distal end of the outer tubular member comprises a coupling mechanism configured to be coupled to a needle. In particular embodiments, the proximal end of the outer tubular member comprises a port configured to be coupled to a vacuum source. In some embodiments, the coupling mechanism and the port are in fluid communication with the outer tubular member and the inner tubular member. In specific embodiments, the biasing member is configured as a coil spring that extends around the outer tubular member.

In certain embodiments, the plurality of slots comprises a plurality of radial slots each at a different distance from the proximal end of the outer tubular member and wherein the plurality of radial slots are coupled via a longitudinal slot. In particular embodiments, when the biasing member is in an expanded configuration the plurality of radial slots comprise: a first slot positioned approximately 0.5 cm from the proximal end of the outer housing; a second slot positioned approximately 1.0 cm from the proximal end of the outer housing; a third slot positioned approximately 2.0 cm from the proximal end of the outer housing; a fourth slot positioned approximately 3.0 cm from the proximal end of the outer housing; and a fifth slot positioned approximately 4.0 cm from the proximal end of the outer housing.

Certain embodiments include a method of performing a fine needle aspiration, the method comprising: obtaining a device for fine needle aspiration comprising: an inner tubular member comprising a proximal end and a distal end; an outer tubular member disposed around the inner tubular member, where the outer tubular member comprises a proximal, a distal end, and a plurality of slots; an outer housing disposed around the outer tubular member, where the outer housing comprises a proximal end and a distal end; a biasing member disposed between the outer tubular member and the outer housing; and a rod coupled to the inner tubular member, and where: the rod extends through the outer tubular member; the rod is configured to be moved from a first slot in the plurality of slots to a second slot in the plurality of slots; the first slot is a first distance from proximal end of the housing; the second slot is a second distance from the proximal end of the housing; and the biasing member is configured to bias the housing away from the rod. In particular embodiments the method includes coupling a needle to a coupling mechanism located near the distal end of the outer tubular member; placing the rod in a desired slot of the plurality of slots, wherein a distance from the desired slot to the proximal end of the outer housing is equivalent to a desired distance of penetration of the needle; placing the needle against a surface of a patient; moving the proximal end of the outer tubular member toward the outer housing until the rod engages the proximal end of the outer housing, thereby penetrating the surface of the patient with the needle to a desired distance of penetration; and withdrawing the needle from the patient.

In some embodiments, the desired distance of penetration is approximately 0.5 cm. In specific embodiments, the desired distance of penetration approximately 1.0 cm. In certain embodiments, the desired distance of penetration approximately 2.0 cm. In particular embodiments, the desired distance of penetration approximately 3.0 cm. In certain embodiments, the desired distance of penetration approximately 4.0 cm.

In particular embodiments, placing the rod in the desired slot comprises: moving the rod in a first radial direction toward a longitudinal slot; moving the rod within the longitudinal slot toward the desired slot; and moving the slot in a second radial direction into the desired slot.

In some embodiments, moving the proximal end of the outer tubular member toward the outer housing comprises overcoming a force exerted by the biasing mechanism on the outer housing and the outer tubular member.

In the following disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

DETAILED DESCRIPTION OF ILLUSTRATIVE EMBODIMENTS

Figure 1:
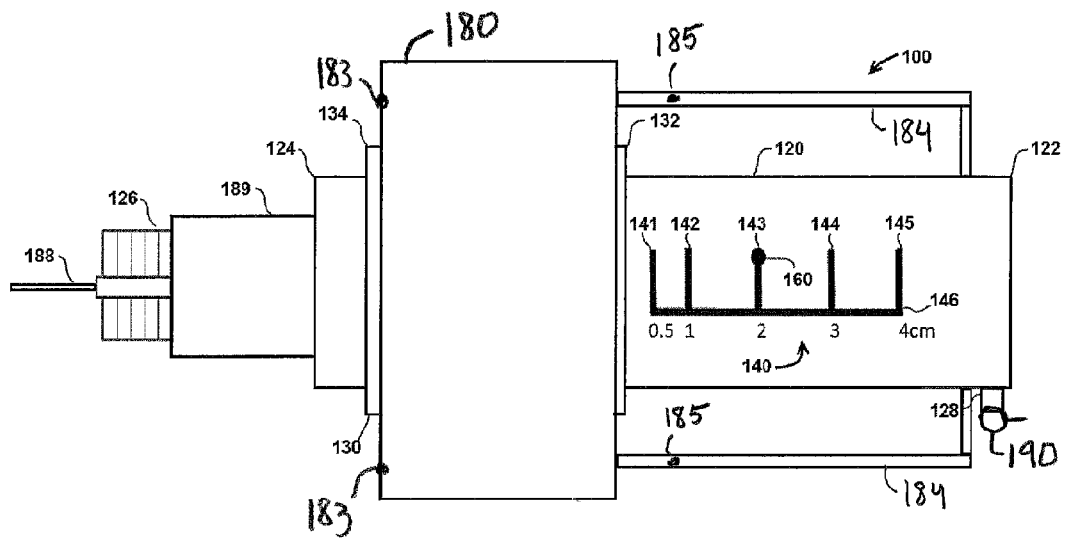
FIG. 1 is a top view of an exemplary embodiment of the present disclosure.
Figure 2:
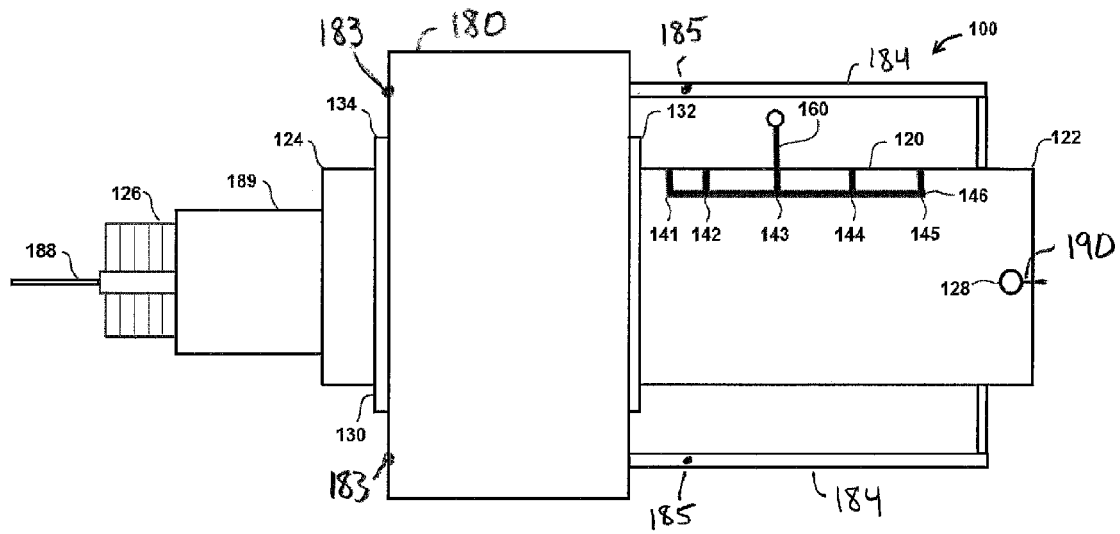
FIG. 2 is a side view of the embodiment of FIG. 1.

Referring to FIGS. 1-4, an exemplary embodiment of a device 100 configured for fine needle aspiration device comprises an inner tubular member 110, an outer tubular member 120 comprising a plurality of slots 140, an intermediate housing 130, and a biasing member 150. In the embodiment shown, outer tubular member 120 is disposed around inner tubular member 110 and biasing member 150 is disposed between outer tubular member 120 and intermediate housing 130.

In this embodiment, inner tubular member 110 comprises a proximal end 112 and a distal end 114, outer tubular member 120 comprises a proximal end 122 and a distal end 124, and intermediate housing 130 comprises a proximal end 132 and a distal end 134. In the embodiment shown, slots 140 comprise radial slots 141-145 each at a different distance from proximal end 122 of outer tubular member 120. In addition, radial slots 141-145 are coupled via a longitudinal slot 146. In this particular embodiment, radial slots 141-145 are positioned approximately 0.5 cm, 1.0 cm, 2.0 cm, 3.0 cm, and 4.0 cm from proximal end 132 of intermediate housing 130.

Figure 3:
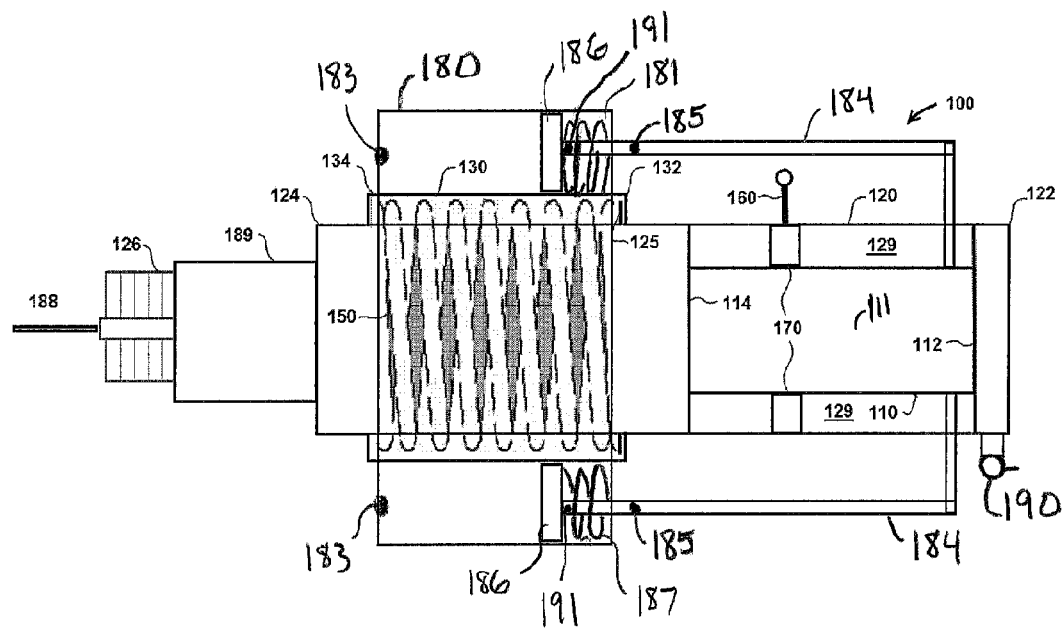
FIG. 3 is a partial section view of the embodiment of FIG. 1 in a first position.
Figure 4:
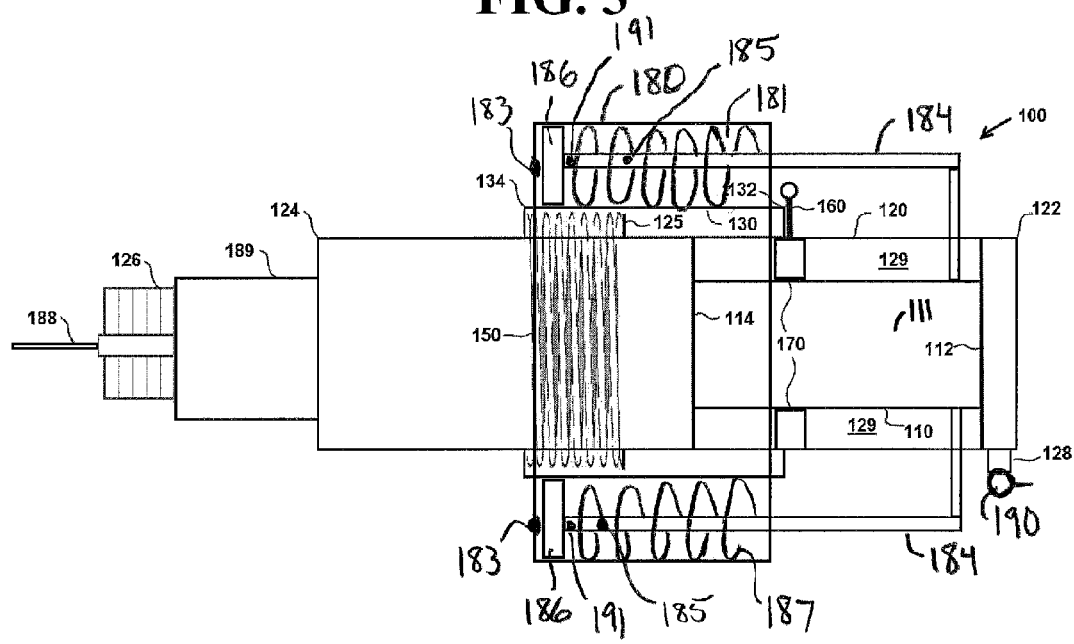
FIG. 4 is a partial section view of the embodiment of FIG. 1 in a second position.

As shown in the partial cross-section views of FIGS. 3-4, device 100 comprises a collar 170 that extends around inner tubular member 110 and is configured for axial and radial sliding engagement with inner tubular member 110. Device 100 further comprises a rod 160 that is coupled to collar 170 and extends through outer tubular member 120 through slots 140. As explained in further detail below, rod 160 can be moved into one of slots 141-145 to adjust the distance between rod 160 and proximal end 132 (of housing 130) to a desired distance. For example, if rod 160 is extending through slot 145 and the user desires to adjust the distance between rod 160 and proximal end 132 to a distance of 1.0 cm, the user can move rod 160 in a first radial direction toward longitudinal slot 146. The user can then move rod 160 along longitudinal slot 146 and into radial slot 143 in a second radial direction away from longitudinal slot 146. In certain embodiments, device 100 may comprise a motorized mechanism configured to move rod 160.

In the embodiment shown, biasing member 150 engages distal end 134 of intermediate housing 130 and a projection 125 that extends from outer housing 120. With biasing member 150 in an expanded configuration shown in FIG. 3, device 100 is configured so that proximal end 132 of intermediate housing 130 engages projection 125. During operation, a user can grip intermediate housing 130 and exert a force on outer tubular member 120 (e.g. in a direction from proximal end 122 toward distal end 124). The application of such a force can compress biasing member 150 and allow outer tubular member 120 to move in a longitudinal (e.g. axial) direction toward intermediate housing 130. Outer tubular member 120 can be moved toward intermediate housing 130 until rod 160 engages proximal end 132 of intermediate housing 130 as shown in the compressed configuration of FIG. 4. The user can control the distance that outer tubular member 120 is allowed to move toward intermediate housing 130 by placing rod 160 into a desired radial slot 141, 142, 143, 144, or 145. In the embodiment shown, for example, a user can control this distance to 0.5 cm, 1.0 cm, 2.0 cm, 3.0 cm or 4.0 cm by placing rod 160 into radial slot 141, 142, 143, 144, or 145, respectively.

In the embodiment shown, distal end 124 of outer tubular member 120 may comprise a coupling mechanism 126 configured to couple an instrument such as a needle (not shown) to distal end 124. In particular embodiments, coupling mechanism may comprise a Luer taper, including for example a Luer-Lock or a Luer-Slip configuration. Depending on the diameter of the configuration, coupling mechanism 126 can be configured so that a needle can be placed directly over threads at one end (with smaller diameters), or coupling mechanism 126 can have knob at the end on which needle can fit (with larger diameters).

In particular embodiments, certain components (e.g. inner tubular member 110, outer tubular member 120, and/or intermediate housing 130) may be formed from a plastic or fiber material that is transparent, semitransparent, or translucent.

During certain procedures a user may place the needle (or other instrument coupled to distal end 124) against a surface of a patient while biasing mechanism 150 is in an expanded configuration. The user can grip intermediate housing 130 while quickly moving proximal end 122 toward intermediate housing 130 until rod 160 engages proximal end 132 of intermediate housing 130. In certain embodiments, the needle will be advanced a distance equivalent to the distance between rod 160 and proximal end 132 of intermediate housing 130, thereby penetrating the surface of the patient with the needle to a desired distance of penetration. The user can then withdraw the needle from the patient.

The ability to precisely control the distance that outer tubular member 120 is allowed to move relative to intermediate housing 130 can provide numerous benefits when performing procedures, including for instance, a fine needle aspiration (FNA). For example, the use of device 100 can allow a user to increase the speed of the instrument excursion, as well as increase the number of excursions and increase the depth of penetration. These advantages can increase the amount of tissue that is obtained by the needle and reduce the amount of blood that contaminates the sample. This can reduce failed FNA attempts and allow FNA procedures to be performed in less time. In addition, the precise depth control of device 100 can allow a user to acquire more specimen material with less blood contamination, which can sometimes obviate need for more invasive core biopsies. The straightforward operation of device 100 can also allow it to be used effectively by both experienced and inexperienced users.

The embodiment shown in FIGS. 1-4 also comprises additional features and components configured to increase the quality and volume of a sample obtained during FNA procedures. For example, device 100 comprises an outer cylinder 180 that extends around inner tubular member 110, outer tubular member 120 and intermediate housing 130. Device 100 also comprises a sealing member or piston 186 disposed between intermediate housing 130 and outer cylinder 180. Piston 186 is coupled to one or more tubular members 184 that are in fluid communication with a portion of interior volume 181 of outer cylinder 180 (e.g. the portion of interior volume 181 that is on the side of piston 186 that is nearest proximal end 122). In addition, tubular members 184 are in fluid communication with an interior volume 111 of inner tubular member 110. In exemplary embodiments, tubular members 184 can be positioned such that they do not restrict access to rod 160. In the embodiment shown, tubular members 184 are configured parallel to the primary axis of device 100. While two tubular members 184 are shown in the illustrated embodiment, it is understood that other exemplary embodiments may comprise a single tubular member 184 or more than two tubular members 184. As explained more fully below, interior volume 111 is in fluid communication with a lumen in needle 188 and reservoir 189. Accordingly, when a vacuum (e.g. reduced pressure) is created in inner volume 111, needle 188 can be used to withdraw material from a subject into reservoir 189.

Tubular members 184 further comprise one or more one-way valve 185 in fluid communication with interior volumes 181 and 111. Accordingly, as piston 186 is moved toward distal end 124, a lower pressure or vacuum is created in a first portion of interior volume 181 of outer cylinder 180 (e.g. the portion of interior volume 181 that is located on the proximal side of piston 186 that is coupled to tubular members 184). In the embodiment shown, one-way valves or orifices 183 are in fluid communication with interior volume 181 and the external atmosphere. One-way valves or orifices 183 are configured to vent pressure from the interior volume 181 to an external atmosphere. For example as piston 186 is moved toward distal end, the pressure will increase in the portion of interior volume 181 that is on the side of piston 186 nearest distal end 124. One-way valves or orifices 183 can vent this pressure to external atmosphere and allow a user to more easily displace piston 186 toward distal end 124.

In particular embodiments, a biasing member or spring 187 may also be positioned within outer cylinder 180 to assist in moving piston 186 toward distal end 124. Spring 187 can be compressed when piston 186 is in the position shown in FIG. 3. In this position, spring 187 can exert a force on piston 186 toward distal end 124 and assist a user in overcoming the pressure differential created in interior volume 181 as piston 186 is moved. In exemplary embodiments, spring 187 can be configured such that the force required to compress spring is less than the force required to compress biasing member 150.

As previously mentioned, one-way valves 185 are in fluid communication with both interior volume 181 of outer cylinder 180 and interior volume 111 of inner tubular member 110. One-way valves 185 are configured so that as the pressure is reduced in a portion of interior volume 181, the pressure will also be reduced in interior volume 111. Certain embodiments may also comprise an orifice 191 in tubular members 184 to allow reduced pressure from interior volume 181 to be transmitted to tubular members 184 and interior volume 111. The lower pressure created in interior volume 111 can assist in drawing material obtained through a lumen of needle 188 coupled to coupling mechanism 126. In certain embodiments, needle 188 is in fluid communication with reservoir 189. In this manner, cells or other material obtained through needle 188 can be stored in reservoir 189, thereby increasing the maximum volume of a sample that can be obtained with device 100. In certain embodiments, reservoir 189 can be removed from device 100, thereby allowing a user easier access to material stored in reservoir 189.

Figure 5:
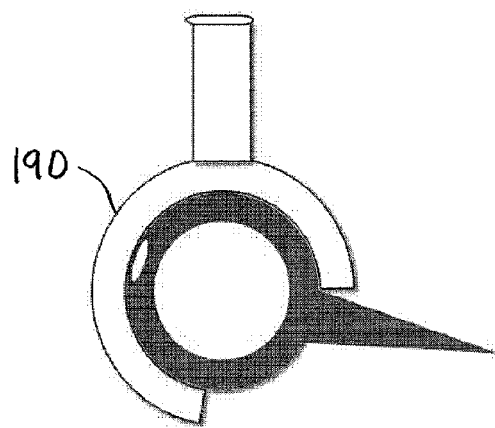
FIG. 5 is a section view of a release valve of the embodiment of FIG. 1 in a first position.

Outer tubular member 120 may further comprise a port 128 near proximal end 122 that is in fluid communication with inner tubular member 110 and coupling mechanism 126. Device 100 can also comprise a release valve 190 in fluid communication with port 128 and interior volume 111. Release valve 190 can be placed in a first position such that interior volume 111 is not in fluid communication with the external environment. In this position, a vacuum can be created within interior volume 111 as previously described. In addition, release valve 190 can be placed in a second position such that interior volume 111 is in fluid communication with the external environment. In this position, the vacuum within interior volume will be released (e.g. the pressure within interior volume 111 will be increase to atmospheric pressure). During operation, release valve 190 can be placed in the first position shown in FIG. 5 when device 100 is being used to obtain material via needle 188. In this position the vacuum created by piston 186 can assist in drawing material through needle 188 and into reservoir 189. In certain embodiments, reservoir 189 may be configured as a 5 mm wide and 1 cm long tube with a female Luer lock at one end and a male Luer lock at top.

Figure 6:
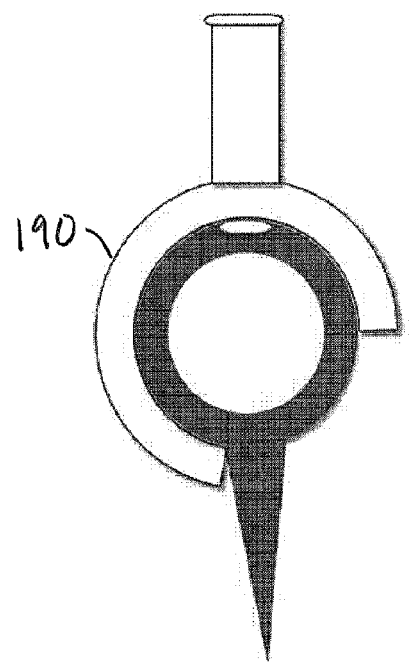
FIG. 6 is a section view of a release valve of the embodiment of FIG. 1 in a first position

When the user desires to break the vacuum (e.g. raise the pressure in interior volume 111), the user can move release valve 190 to the second position shown in FIG. 6. In exemplary embodiments, release valve 190 can positioned opposite rod 160 to allow for ease of operation of device 100. For example, release valve 190 can be configured such that the lever used to actuate the release valve can be operated with the same hand used to insert needle 188 into a subject, thereby allowing device 100 to be operated with one hand.

After release valve 190 has been operated to release the vacuum within interior volume 111), a user can return piston 186 the position shown in FIG. 3. The user can also then return release valve to the position shown in FIG. 5. Device 100 will then be in position to create a vacuum within interior volume 111 to assist in obtaining material. In certain embodiments, device 100 may be configured to be re-usable such that certain components can be replaced (e.g. needle 188, coupling mechanism 126, and/or reservoir 189). In other embodiments, device 100 may be configured as a disposable device such that the entire device is discarded after use.

Figure 7:
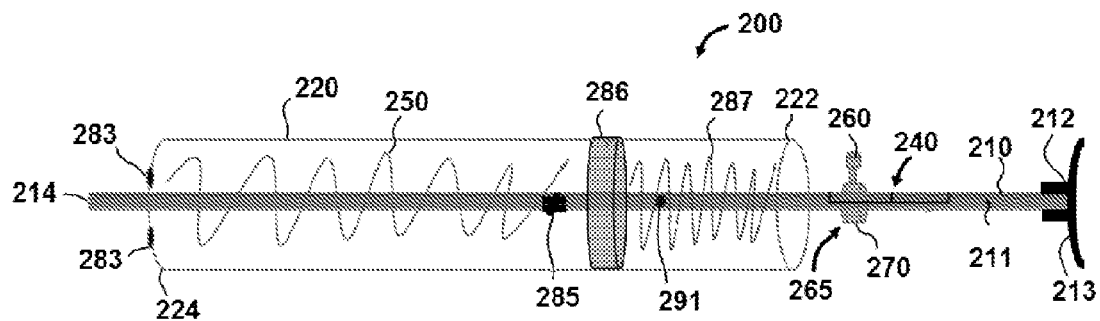
FIG. 7 is a partial section view of an exemplary embodiment of the present disclosure.
Figure 8:
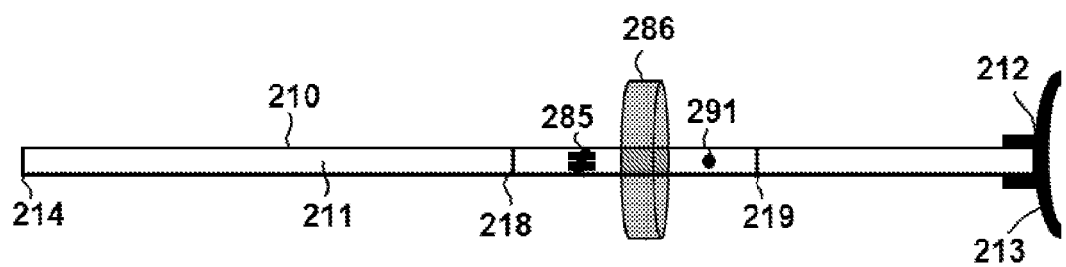
FIG. 8 is a side view of components of the embodiment of FIG. 7.

Referring now to FIGS. 7 and 8, an exemplary embodiment of a device 200 configured for fine needle aspiration operates under similar principles to the previously-described embodiment but includes fewer components. Where possible, similar components have been identified with reference numbers similar to the previously-described embodiment but beginning with the numeral "2" (e.g. the piston in the embodiment of FIGS. 7 and 8 is identified by reference number 286, while the piston in the previously-described embodiment is identified by reference number 186).

Device 200 comprises an inner tubular member 210 with an interior volume 211, an outer cylinder 280 with an interior volume 281. Device 200 further comprises a piston 286, a first biasing member 250 and a second biasing member 287. In certain embodiments, inner tubular member 210 may comprise multiple parts that can be coupled together at joints 218 and 219 to allow easier assembly (as shown in FIG. 8). In particular embodiments biasing members 250 and 287 may be configured as a coil spring or other suitable biasing member configured to act on piston 286. Biasing members 250 and 287 bias piston 286 toward a central location as illustrated in FIG. 7. In the embodiment shown, outer cylinder 280 comprises a proximal end 222 and a distal end 224, while inner tubular member 210 comprises a proximal end 212 and a distal end 214. Outer cylinder 280 further comprises orifices 283 near distal end 224.

A depth control mechanism 265 is coupled to inner tubular member 210 near proximal end 222. Depth control mechanism 265 comprises a collar 270 and locking member 260 (e.g. a threaded bolt or screw that extends through collar 270 and can be tightened to secure collar 270 at the desired location on inner tubular member 210). In the embodiment shown, inner tubular member 210 comprises depth indications 240 in the region of collar 270 and proximal end 222 of outer cylinder 280. Depth indications 240 can be marked at desired intervals (e.g. 1, 2 and 3 centimeters) to indicate the location at which collar 270 can be secured to inner tubular member 210 to allow for the desired depth of movement between inner tubular member 210 and outer cylinder 280 during operation. A gripping mechanism 213 can be coupled to inner tubular member 210 near proximal end 212 to assist in moving inner tubular member with respect to outer cylinder 180.

In addition, inner tubular member 210 comprises an orifice 291 between piston 286 and proximal end 222 of outer tubular member. Inner tubular member 210 further comprises a one-way valve 285 configured to allow fluid (e.g. air) through inner tubular member in a direction away from distal end 224 and toward proximal end 222 of outer cylinder 280.

In preparation for operation, a user can set depth control mechanism 265 at the desired location by securing collar 270 in the desired location. The user can then push gripping mechanism 213 and proximal end 212 of inner tubular member 210 toward outer cylinder 280. The movement of piston 286 toward distal end 224 of outer cylinder 280 creates a suction or negative pressure in the portion of the interior volume of outer cylinder 280 between piston 286 and proximal end 222. The negative pressure is transmitted to the interior volume of inner tubular member 210 via orifice 291. One-way valve 285 within inner tubular member 210 permits fluid flow created by the negative pressure to flow from distal end 214 toward proximal end 212 of inner tubular member.

Figure 9:
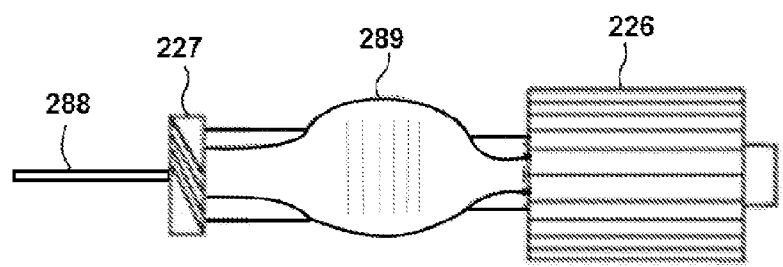
FIG. 9 is a side view of a coupling mechanism configured to couple to the embodiment of FIG. 7.

In certain embodiments, device 200 can be coupled to a reservoir and needle via one or more coupling mechanisms. Referring now to FIG. 9, a reservoir 289 can be coupled to device 200 via a coupling mechanism 226, and a needle 288 can be coupled to reservoir 289 via a coupling mechanism 227. In exemplary embodiments, coupling mechanisms 226 and 227 may be configured as a Luer Lock mechanisms, including for example a Luer-Lock or a Luer-Slip configuration. In the embodiment shown in FIG. 9, reservoir 289 is shaped with curved sides to prevent residue from getting trapped inside reservoir during operation. It is understood that the previously-described embodiment in FIGS. 1-4 may also comprise a reservoir with curved sides to prevent residue from getting trapped inside reservoir during operation.

Similar to the principles of operation of the previously-described embodiment, interior volume 211 is in fluid communication with a lumen in needle 288 and reservoir 289 when coupling mechanism 226 is coupled to device 200. Accordingly, when a vacuum (e.g. reduced pressure) is created in inner volume 211, needle 288 can be used to withdraw material from a subject into reservoir 289.

In particular embodiments, certain components (e.g. inner tubular member 210 and outer cylinder 280) may be formed from a plastic or fiber material that is transparent, semitransparent, or translucent.

Exemplary embodiments disclosed herein are believed to significantly increase the amount of tissue or other material obtained during a FNA procedures. In certain embodiments, it is believe that the suction mechanism can increase yields by up 100 times the amount of material obtained without the aid of suction.

It is understood that the above-described methods are merely examples of the procedures capable of being performed with exemplary embodiments of the devices disclosed herein.

All of the apparatus, devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 4,697,600
U.S. Pat. No. 4,766,907
U.S. Pat. No. 5,916,175
U.S. Pat. No. 5,951,489
U.S. Pat. No. 6,402,701
U.S. Pat. No. 7,037,276
U.S. Pat. No. 7,766,843
U.S. Pat. No. 7,927,288
U.S. Patent Publication 2002/0082518
U.S. Patent Publication 2005/0228312
U.S. Patent Publication 2013/0060160
U.S. Patent Publication 2013/0165815
U.S. Patent Publication 2013/0172777
European Patent 0983749
European Patent 0983021

The invention claimed is:

1. A device for fine needle aspiration, the device comprising:
an inner tubular member comprising a proximal end and a distal end;
a sealing member coupled to the inner tubular member;
an outer cylinder comprising a proximal end and a distal end, wherein the outer cylinder is disposed around the inner tubular member and the sealing member;
a first orifice in a surface of the inner tubular member; and
a one-way valve in fluid communication with the inner tubular member wherein:
the first orifice in the surface of the inner tubular member is located between the sealing member and the proximal end of the inner tubular member; and
movement of the sealing member towards the distal end of the outer cylinder creates a vacuum in the inner tubular member.

2. The device of claim 1 further comprising a depth control mechanism coupled to the inner tubular member.

3. The device of claim 2 wherein:
the depth control mechanism comprises a collar and a locking member; and
the locking member can secure the collar at a desired location on the inner tubular member.

4. The device of claim 3 further comprising depth indications on the inner tubular member.

5. The device of claim 4 wherein the depth indications are at intervals to indicate the location at which the collar can be secured to the inner tubular member to allow for a desired depth of movement between the inner tubular member and the outer cylinder.

6. The device of claim 1 further comprising a first biasing member and a second biasing member, wherein the first biasing member and the second biasing member are configured to bias the sealing member toward a central location within the outer cylinder.

7. The device of claim 1 wherein the outer cylinder further comprises a second orifice near the distal end of the outer cylinder.

8. The device of claim 1 wherein the inner tubular member is configured to be assembled with a plurality of components coupled at one or more joints.

9. The device of claim 1 further comprising a gripping mechanism coupled to the inner tubular member near the proximal end.

10. The device of claim 1 wherein the inner tubular member comprises an interior volume and wherein the device further comprises a needle in fluid communication with the interior volume of the inner tubular member.

11. The device of claim 10 further comprising a reservoir in fluid communication with the interior volume of the inner tubular member and the needle.

12. A device for fine needle aspiration, the device comprising:
an inner tubular member comprising a proximal end and a distal end;
a sealing member coupled to the inner tubular member;
an outer cylinder comprising a proximal end and a distal end, wherein the outer cylinder is disposed around the inner tubular member and the sealing;
a first biasing member and a second biasing member, wherein the first biasing member and the second biasing member are configured to bias the sealing member toward a central location within the outer cylinder;
a depth control mechanism configured to allow a desired depth of movement between the inner tubular member and the outer cylinder;
a one-way valve in fluid communication with the inner tubular member wherein:
the first orifice in the surface of the inner first tubular member is located between the sealing member and the proximal end of the inner tubular member; and
movement of the sealing member towards the distal end of the outer cylinder creates a vacuum in the inner tubular member.

13. The device of claim 12 wherein the inner tubular member comprises an interior volume and wherein the device further comprises a needle in fluid communication with the interior volume of the inner tubular member.

14. The device of claim 13 further comprising a reservoir in fluid communication with the interior volume of the inner tubular member and the needle.

15. A method of fine needle aspiration, the method comprising:

obtaining a device configured for fine needle aspiration, wherein the device comprises:
- an inner tubular member comprising a proximal end, a distal end and an interior volume;
- a sealing member coupled to the inner tubular member;
- an outer cylinder comprising a proximal end and a distal end, wherein the outer cylinder is disposed around the inner tubular member and the sealing member;
- a depth control mechanism configured to allow a desired depth of movement between the inner tubular member and the outer cylinder;
- a needle coupled to the inner tubular member, wherein the needle is in fluid communication with the inner tubular member;
- an orifice in a surface of the inner tubular member, wherein the orifice is located between the sealing member and the proximal end of the inner tubular member;

setting the depth control mechanism to allow the desired depth of movement between the inner tubular member and the outer cylinder;

placing the needle against a surface of a patient;

pushing the proximal end of the inner tubular member toward the outer cylinder, wherein the needle penetrates the surface of the patient the desired depth of movement;

creating a vacuum in a portion of the outer cylinder between the sealing member and the distal end of the outer cylinder, wherein the vacuum is transmitted to the interior volume of the inner tubular member via the orifice in the surface of the inner tubular member; and withdrawing tissue from the patient through the needle.

16. The method of claim 15 wherein the vacuum is used to assist in withdrawing material through a lumen of the needle in fluid communication with the inner tubular member.

17. The method of claim 16 further comprising storing the material in a reservoir in fluid communication with the lumen of the needle.

18. The method of claim 16 wherein the material is a tissue sample.

* * * * *